US000001056H

United States Statutory Invention Registration [19]

[11] Reg. Number: H1056

Bernard

[43] Published: May 5, 1992

[54] TRIPEPTIDE, ITS PREPARATION AND USE

[76] Inventor: Jean-Marie Bernard, Route du Large - Saint Laurent d'Agny, 69440 - Mornant, France

[21] Appl. No.: 527,928

[22] Filed: May 24, 1990

[30] Foreign Application Priority Data

May 24, 1989 [FR] France ..... 89 06777

[51] Int. Cl.[5] ..... C07K 5/00
[52] U.S. Cl. ..... 530/333
[58] Field of Search ..... 530/331

[56] References Cited

U.S. PATENT DOCUMENTS 4,242,256 12/1980 Sharpe et al. ..... 530/328
4,954,616 9/1990 Callens et al. ..... 530/333

OTHER PUBLICATIONS

Gross et al., eds., *The Peptides*, 1980, vol. 2, pp. 101–103, 106–114, 118, and 169–173.

Gross and Meienhofer, "Reversible Blocking of Amino and Carboxyl Groups," The Peptides, vol. 3, Chapter III, pp. 59–118 (Academic Press 1981).

*Primary Examiner*—Richard D. Lovering
*Assistant Examiner*—Joseph D. Anthony

[57] ABSTRACT

A tripeptide having the following composition:

Leucyl - Arginyl - Proline as well as a process for its preparation. The tripeptide may contain protecting groups on at least one of the amine functions and on the C-terminal acid function.

10 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

TRIPEPTIDE, ITS PREPARATION AND USE

The present invention concerns a tripeptide its preparation and use. This tripeptide is an intermediate compound in an important synthesis, i.e., preparation of hormone permitting of the liberation of luteinizing hormone, which is also known by the abbreviation LHRH.

The LHRH hypothalamic hormone functions to regulate the secretion of gonadotrophic hormones. Because of the demand for it on a clinical level, numerous derivatives of the latter have been synthesized. The majority of these compounds involve, in the interior of their molecules, the tripeptide of the present invention, which has never, to the inventor's knowledge, previously been synthesized. This tripeptide, which is thus novel and is the object of the present application, has the following formula:

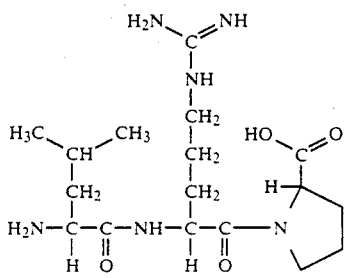

The tripeptide of the invention is more commonly known as Leucyl-Arginyl-Proline. The tripeptide can also be protected on at least one of its acid and/or amine functions by one or more conventional protecting groups used in peptide synthesis, particularly such as those described by Gross and Meienhofer (The Peptides, Volume 3, Academic Press 1981), specifically incorporated by reference herein.

Representative protecting groups of the amine function include the following groups:

t-butyloxycarbonyl which is known by the abbreviation BOC benzyloxycarbonyl, which is known by the abbreviation Z fluorenylmethoxycarbonyl, which is known by the abbreviation FMOC benzoyl fluoracetyl triofluoroacetyl urethane formyl trityl and nitrophenylsulphenyl ($NO_2$—$\phi$—S(O)—).

Illustrative protecting groups for the C-terminal acid function include:

ester groups, particularly alkyl esters whose alkyl chains contain from 1 to 20 carbon atoms, more particularly methyl, ethyl, phenyl, benzyl and t-butyl esters; and amide groups, which may either be primary or substituted on the nitrogen atom.

The tripeptide that forms the object of the present invention is prepared by a procedure that comprises:

in a first step (a), putting L-nitroArginine, protected on the amine function thereof into contact with L-Proline protected on the acid function thereof in the presence of an activator and at least one base in a solvent for a time sufficient to obtain L-nitroArginyl-L-Proline dipeptide containing protecting groups;

in a second step (b) hydrogenating the dipeptide obtained in the first step in a manner and for a time sufficient to eliminate the protecting group of the Arginine and the protecting group of the Proline, and also to reduce the nitro radical on the L-nitroArginyl portion of the dipeptide; and in a third step (c) putting the dipeptide resulting from the second step into contact in a solvent with L-Leucine protected on its amine function in the presence of an activator, at least one base and an auxiliary nucleophile for a time sufficient to obtain the compound of claim 1.

The protecting group of one of the amine functions of the L-nitroArginine is preferably a benzyloxycarbonyl group, the group protecting the second amine function is preferably a nitro group and the group protecting the acid function of the Proline is preferably a benzyl group.

The group protecting the amine function of the L-Leucine is also preferably a benzyloxycarbonyl group.

During the first step (a), the substeps of activation of the protected L-nitroArginine, condensation and separation may be carried out. The condensation activator may be selected from among the following compounds:

alkanoic aralkanoic and aroic acid chlorides phosphoric acid anhydrides carbodiimides and active esters.

Illustrative condensation activators include:

pivaloyl chloride dimethoxytriazine chloride

Castro reactant (BOP)

isobutyl chloroformate and cyclohexylcarbodiimide (DCC).

It is preferred to use pivaloyl chloride.

The use, for example, of dimethoxytriazine chloride in slight excess with respect to the Arginine can cause the formation of an intermediate protected dimethoxytriazine-proline which is decomposed as the reaction proceeds.

The use of dicyclohexylcarbodiimide can result in the appearance of a substantial precipitate of dicyclohexylurea, which can be difficult to separate, and thus is not preferred.

The molar ratio of the activating agent and the protected Arginine in step (a) preferably ranges from 1:1 to 1.5:1. The molar ratio of the L-Proline to the L-nitroArginine in step (a) preferably ranges from 1:1 to 2:1.

The at least one base for activating and causing condensation in step (a) is preferably selected from tertiary nitrogen bases and alkali metal bases. Preferred bases include: N-methyl-morpholine, triethylamine, sodium carbonate and diisopropylethylamine.

For the activation substep in step (a), the base is preferably selected from amines that are soluble in organic media and that do not present a basicity so high that racemization of the Arginine could occur. It is therefore preferred to use hindered tertiary amine bases such as N-methylmorpholine, diisopropylethylamine and N-methylpiperidine.

The molar ratio of the base to the L-nitroArginine in the activation substep in step (a) preferably ranges from 1:1 to 2:1.

For the condensation substep in step (a), the hydrochloride of the protected proline is displaced, preferably with a relatively strong base having a pK greater than that of the protected proline. It is therefore preferable to use a base in the condensation substep in step (a) selected from triethylamine and sodium bicarbonate.

The molar ratio of the base to the L-Proline in the condensation substep in step (a) preferably ranges from 1:1 to 2:1.

The solvent used in the activation and condensation substeps of step (a) is preferably selected from dichloromethane, ethyl acetate, dioxane, tetrahydrofuran, dimethylformamide, t-butanol, toluene and dimethoxyethane. It is preferred to use dichloromethane.

The reaction temperature used during the activation substep and during the coupling (condensation) substep of step (a) preferably ranges from −30° to 40° C. and more preferably ranges from −15° C. to ambient temperature.

To complete the first step (a), the protected arginyl-proline dipeptide may be washed and then separated, for example, by crystallization from ethyl acetate.

The second step (b) consists of eliminating the protecting groups carried by the Arginine and the Proline and also in reducing the nitro group carried by the Arginine portion of the dipeptide. This double reaction is carried out by hydrogenation of the Arginyl-Proline dipeptide containing protecting groups in an acidic medium.

The hydrogenation of the second step may be carried out in the presence of a catalyst based on a noble metal, i.e., nickel, palladium or platinum, deposited on an inert support and in the presence of a mineral or organic acid. The noble metal is preferably palladium deposited on carbon.

It is preferable to use a quantity by weight of noble metal from 0.5 to 5% with respect to the dipeptide, which corresponds to about 5 to 50% by weight of supported catalyst with respect to the weight of the dipeptide.

The hydrogenation is preferably carried out in a solvent made up of a mixture of carboxylic acid and water also containing at least two equivalents of a strong acid. Each equivalent of strong acid can block the presence of guanidine and primary amine functions in the form of salts, thereby avoiding the formation of diketopiperazine.

The acid used in step (b) is preferably selected from hydrochloric acid, hydrobromic acid, sulfuric acid, p-toluenesulphonic acid and methanesulphonic acid. It is preferred to use hydrochloric acid.

As noted above, the solvent preferably used in step (b) is made up of a mixture of carboxylic acid and water, and more preferably is a mixture of acetic acid and water containing 90% by volume of acetic acid.

The hydrogen pressure used in step (b) advantageously ranges from 1 to 20 bars and more preferably from 1 to 5 bars.

The reaction temperature in step (b) preferably ranges from 0° to 100° C. and more preferably from ambient temperature to 50° C.

The unprotected Arginyl-Proline dipeptide obtained in step (b) may be purified and separated by crystallization in ethyl acetate.

The third step (c) of the procedure according to the invention consists of condensing the Arginyl-Proline dipeptide with Leucine.

This condensation may be carried out in three substeps:

a substep of activating the leucine;

a substep of condensing on the dipeptide; and a substep of separation.

The substep of activation in step (c) is carried out by adding an activating agent preferably selected from isobutyl chloroformate and pivaloyl chloride.

Activating agents that are too onerous (Castro reagent), do not yield good results (methoxytriazine chloride) or involve the formation of secondary products that are difficult to separate (dicyclohexylcarbodiimide) are not preferred.

The preferred isobutyl chloroformate and pivaloyl chloride activators are only slightly onerous compounds and give only small quantities of secondary products, which are easily eliminated by crystallization.

The molar ratio of the activating agent to the L-Leucine in the activation substep of step (c) advantageously ranges from 0.5:1 to 1:1.

Formation of a mixed anhydride (pivaloyl-protected Leucine or isobutyl-protected Leucine) is helped in the activation substep of step (c) by the presence of a weak activating base, preferably selected from hindered tertiary amines such as N-methylmorpholine and diisopropylethylamine. The molar ratio of the base to the Leucine advantageously ranges from 1:1 to 2:1.

The mixed anhydride is displaced by using an auxiliary nucleophile which serves to avoid the formation of a mixed anhydride between the protected Leucine and the Arginyl-Proline dipeptide (Z Leu-Arg-Pro-CO-O-CO-Leu-Z) by attack on the dipeptide Arg-Pro or tripeptide Leu-Arg-Pro carboxylate on the activated and protected Leucine.

Illustrative auxiliary nucleophiles include:

hydroxybenzotriazole hydroxysuccinimide thiazolidine-thiol which has the formula

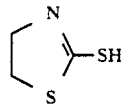

3-hydroxy-3,4-dihydro-1,2,3-benzotriazine-4-one, which has the formula

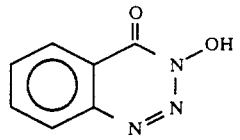

The use of hydroxybenzotriazole is preferred.

The molecular ratio of the auxiliary nucleophile to the Leucine advantageously ranges from 0.1:1 to 2:1 and preferably from 0.8:1 to 1.2:1.

The activation reaction in step (c) is carried out in the same solvents and under the same conditions as those described for the activation substep of the first step (a) of the process in accordance with the invention. It is preferred, however, to use dichloromethane or dimethylformamide at a temperature of around −15° C.

The condensation substep of step (c) may be carried out by introducing, into the medium containing the activated Leucine, the dipeptide in solution in a solvent selected from dimethylformamide, dichloromethane, trifluoroethanol, acetic acid, isopropanol, tetrahydrofuran, acetonitrile and dimethoxyethane. It is preferred to use a solvent made up of dimethylformamide and water.

The base used for the condensation substep of step (c) is preferably selected from sodium bicarbonate, triethylamine, tributylamine, and sodium acetate. The molar ratio of the base to the Leucine in the condensation substep of step (c) advantageously ranges from 1:1 to 4:1, and more preferably from 1.5:1 to 2.5:1.

The condensation temperature advantageously ranges from −30° to 50° C., and more preferably from 0° C. to ambient temperature. The molar ratio of activated Leucine to dipeptide in the condensation substep of step (c) advantageously ranges from 1.5:1 to 2:1.

The tripeptide obtained in step (c) may be extracted, preferably by a mixture of ethyl acetate and butanol, or more generally by a mixture of ester and alcohol that is not miscible with water. The tripeptide may then be concentrated and precipitated by taking the medium up in isopropanol and pouring it into isopropyl ether.

The present invention will be more completely described with the aid of the following Examples, which must not be considered as limiting the invention.

Example of the First Step (a) of the Procedure

Method of Operation

At ambient temperature in a three-necked 250 ml flask are placed successively 19 g of Z-Arg ($NO_2$)-COOH, 95 ml of methylene chloride and 5.82 ml of N-methylmorpholine. The mixture is stirred for five minutes and then cooled to −5° C.

6.5 ml of pivaloyl chloride are added over ten minutes, while the temperature is maintained constant at −5° C. The homogeneous reaction mixture is stirred for two hours at −5° C. and becomes orange in color.

15.8 g of powdered hydrochloride of the benzyl ester of L-Proline are added to the reaction mixture.

Then 8.8 ml of triethylamine is added over ten minutes in a manner such that the temperature of the reaction mixture is maintained at −5° C. (the reaction is exothermic).

After two hours of reaction at −5° C., the reaction mixture is taken to a volume of 300 ml by adding 30 ml of diisopropyl ether and adding methylene chloride. Extraction is then conducted.

The organic phase is washed successively with 100 ml of water, 100 ml of 2.5 M potassium bicarbonate, three times with 50 ml of 2.5 M potassium bicarbonate, four times with 50 ml of N hydrochloric acid and finally with water until the pH of the aqueous phase is equal to 5.

The organic solution is concentrated to 100 ml, and 400 ml of ethyl acetate is added with slow stirring. After fifteen minutes, crystallization of the dipeptide begins. The product is maintained in the cold for one night and filtered over a No. 3 fritted glass filter. The precipitate is washed with 50 ml of ethyl acetate and then dried under increasing vacuum.

Results

The pivaloyl chloride enables the desired product to be obtained in a good yield and at good purity. The use of dichloromethane as a solvent permits a harmonious succession of reaction, extraction and crystallization. The concentration is 20% at the beginning and 30% at the end (the Proline is added in powder form). Ethyl acetate permits a substantially complete crystallization of the product and elimination of the impurities formed.

Weight obtained: 24.3 g

Melting point: 147° to 148° C.

[$\alpha_D$=60 (C=1MeOH)

Rate of transformation of Z-Arg ($NO_2$) COOH=92%

Yield based on Arginine introduced to the Z-Arg ($NO_2$)ProBzl=82%

Amount of Z-Arg ($NO_2$)-ProBzl in the filtrate after crystallization=0.3%

Supplementary tests have been carried out by changing the condensation activating agent: they are reported in Table 1.

Method of Operation 21 g of Z-Arg($NO_2$)-Pro-Bzl and 80 ml of acetic acid are introduced into three-necked 250 ml round-bottom flask.

The solution is stirred until the solids have completely dissolved. Then 8 ml of water, 8 g of 10% palladium on carbon and 3.12 ml of 37% aqueous HCl are added to the reaction medium. After purging with nitrogen, hydrogen is bubbled through at ambient temperature over forty-eight hours, with vigorous stirring.

After purging the reactor over a three hour period, the solution is filtered on two Millipore filters (LC and LS) WP of porosity 10 microns and microns. The palladium is rinsed with 2×25 ml of distilled water, and the solution is concentrated. 100 ml of water and then 3.12 ml of aqueous HCl are added and the mixture is concentrated under vacuum. The residue is taken up once in 100 ml of bidistilled water. Then the residual water is removed by addition of 100 ml of absolute ethanol and codistilled until dryness. This last operation is then repeated an additional time. The residue obtained is taken up in 300 ml of a 50:50 (by volume) solution of methanol and ethyl acetate, then poured into one liter of ethyl acetate to obtain a white precipitate which is filtered over a No. 3 fritted glass filter. The precipitate is washed with 100 ml of ethyl acetate and dried under increasing vacuum over $P_2O_5$ at ambient temperature.

Results

Mass obtained: 12.3 g

Rate of transformation of Z-Arg($NO_2$)Pro-Bzl=100%

Yield of Arg-Pro.2HCl=99.3%

Example of the Third Step (c) of the Procedure

Method of Operation 5.13 g of Z-L-Leucine and 40 ml of dimethylformamide are successively placed in a three-necked 250 ml round-bottom flask. The clear solution is stirred and then cooled to −15° C. 2.06 ml of N-methylmorpholine is added (the reaction is slightly exothermic). After five minutes, 2.25 ml of isobutyl chloroformate is added while the temperature is maintained at −15° C.; the whitish reaction mass is maintained for ten minutes at −15° C. and then N-hydroxybenzotriazole is added. After twenty minutes at −15° C. the reaction medium is brought to 0° C. After thirty minutes at 0° C. a solution of 5.8 g of Arg-Pro and 2.44 g of sodium bicarbonate in a mixture of 32 ml of dimethylformamide and 8 ml of water is added. The reaction is exothermic and the temperature is maintained at 0° C. over forty-five minutes. The mixture is then allowed to return to ambient temperature.

After an additional two hours and thirty minutes under these conditions, the reaction continues further and the dimethylformamide is concentrated under increasing vacuum. The oily residue is taken up in 50 ml of water and the excess of Z-Leucine is eliminated by washing with 2×25 ml of isopropyl ether. This extraction enables a part of the hydroxybenzotriazole to be removed.

The aqueous solution is left in the cold for one night. A part of the precipitate of hydroxybenzotriazole is removed by filtration. The remainder is extracted by several washings with diisopropyl ether (5×50 ml). The desired product is extracted with a 50:50 mixture (by volume) of ethyl acetate and n-butanol.

The organic phase is then washed twice with 10 ml of N HCl, then twice with 15 ml of water.

The organic phase is then concentrated under vacuum at 30° C. The viscous oil obtained is taken up in 50 ml of warm isopropanol (50° C.) and poured into 300 ml of isopropyl ether to obtain a white precipitate which is filtered and dried under increasing vacuum.

Results

Quantity obtained: 5.5 g

Yield isolated =70%

Table 2 contains examples of varying the activating agents, solvents, auxiliary nucleophiles and other conditions, along with the results obtained from each.

The process of invention also comprises the step of hydrogenating L-nitroArginyl-L-Proline dipeptide containing protecting groups in an acid medium for a time sufficient to eliminate the protecting groups and to reduce the nitro radical in the L-nitroArginine portion of the dipeptide.

Further, the invention is directed to a process comprising the step of hydrogenating an L-nitroArginyl-L-Proline dipeptide - containing aromatic amino acid, wherein said L-nitroArginyl-L-Proline dipeptide contains protecting groups, in an acid medium for a time sufficient to eliminate the protecting groups and to reduce the nitro radical in the L-nitroArginine portion of the dipeptide.

Notably, the claimed invention can be used in synthesizing polypeptide-containing aromatic amino acids. Illustrative amino acids include dihydroxyphenylalanine, tyrosine, phenylalanine and particularly, tryptophan. In particular, in accord with the present invention, an L-nitroArginyl-L-Proline moiety containing protecting groups can be bonded to a compound containing a aromatic amino-acid. Then, in accord with the hydrogenation step explained above, the nitroArginyl portion of the peptide can be reduced for a time sufficient to eliminate the protecting groups on the L-nitroArginyl-L-Proline portion of the molecule and also to reduce the nitro radical in the L-nitroArginyl portion of the molecule.

TABLE 1

| SAMPLE NO. | REAGENT | RATIO ProBzl/ Z—ArgNO$_2$ | ACTIVATION TIME | RATE OF TRANSFORMATION OF Z—Arg NO$_2$ | YIELD/ Z—Arg NO$_2$ | IDENTIFIED IMPURITIES |
|---|---|---|---|---|---|---|
| 1-2 | 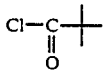 | 1.2 | 2 h at −5° C. 40 min at 0° C. | >95% | 66.5% | Lactam/Piv—Pro Bzl* |
| 1-3 | 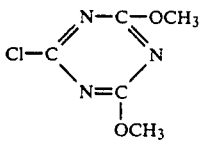 | 1.05 | 3 h at −5° C. | — | 53% | Lactam-DT—Pro Bzl* |
| 1-4 | 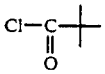 | 1.2 | 1.5 h at −5° C. | 97.5% | 87.5% | Lactam (slight) |
| 1-5 | BOP* | 1 | Ambient Temperature | — | 72% | — |
| 1-6 | BOP* | 1 | Ambient | — | 85.4% | — |

TABLE 1-continued
| SAMPLE NO. | REAGENT | RATIO ProBzl/ Z—ArgNO$_2$ | ACTIVATION TIME | RATE OF TRANSFORMATION OF Z—Arg NO$_2$ | YIELD/ Z—Arg NO$_2$ | IDENTIFIED IMPURITIES |
|---|---|---|---|---|---|---|
| | | | Temperature | | | |
*Impurities:
Lactam:
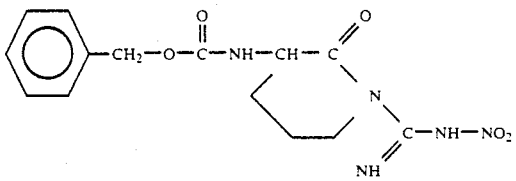
Piv—Pro Bzl:
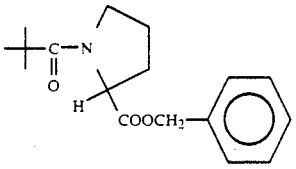
Dimethoxytriazine Pro Bzl:
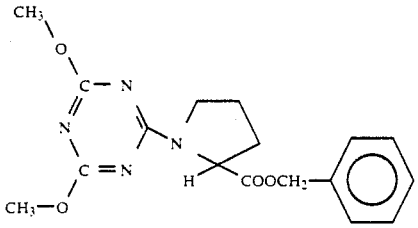
Castro's reagent (BOP):
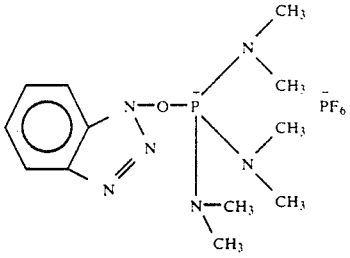

TABLE 2

| SAMPLE NO. | Ratio AM/Z—Leu Arg—Pro 2HCl | ACTIVATION SOLVENT & TEMPERATURE | ACTIVATION BASE | ACTIVATION REAGENT | Arg-Pro.2HCl NEUTRALIZATION BASE | Arg.Pro. 2HCl SOLVENT SOLUTION | AUXILLIARY NUCLEOPHILE | YIELD Z—Leu Arg—Pro | RATE OF TRANSFOR-MATION | PURITY (by HPLC) |
|---|---|---|---|---|---|---|---|---|---|---|
| 3-1 | 1.3 | DMF - 15° C.<br>1h - 5° C. | NHM | 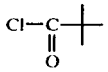 | $NaHCO_3$<br>2 eq. | $DMF/H_2O$<br>90/10 | | 59% | incomplete | 81% |
| 3-2 | 1.7 | $CH_2Cl_2$ - 5° C.<br>30 mn - 5° C. | NHM | 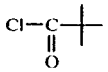 | $NaHCO_3$<br>2 eq. | $DMF/H_2O$<br>80/20 | 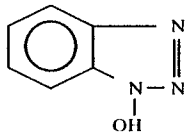 | 27% | 68% | |
| 3-3 | 1.65 | DMF - 5° C. | NMM | 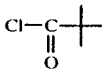 | $NaHCO_3$<br>2 eq. | $DMF/H_2O$<br>80/20 | 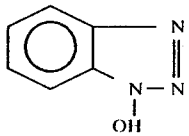 | 70% | 100% | |
| 3-4 | 1.16 | DMF - 5° C. | NMM | 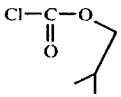 | $NaHCO_3$<br>2 eq. | $DMF/H_2O$<br>80/20 | | 79% | 100% | |
| 3-5 | 1.15 | DMF - 5° C. | NMM | 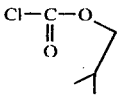 | $NaHCO_3$<br>2 eq. | $DMF/H_2O$<br>80/20 | 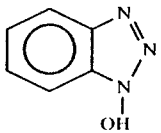 | 89%<br>(dose) | 97.5% | |
| 3-6 | 1.3 | DMF - 15° C. | NMM | 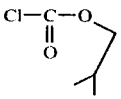 | $NaHCO_3$<br>2 eq. | $DMF/H_2O$<br>80/20 | 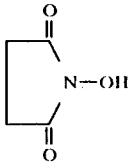 | 67.5% | 75% | 89.5% |
| 3-7 | 1.2 | DMF - 15° C. | NMM | 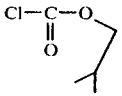 | NHM<br>2 eq. | DMF | 2 eq.<br>$Cl—SiMe_3$<br>Arg—Pro | 77% | 100% | 84% |

TABLE 2-continued

| SAMPLE NO. | Ratio AM/Z—Leu Arg—Pro 2HCl | ACTIVATION SOLVENT & TEMPERATURE | ACTIVATION BASE | ACTIVATION REAGENT | Arg-Pro.2HCl NEUTRALIZATION BASE | Arg.Pro. 2HCl SOLVENT SOLUTION | AUXILLIARY NUCLEOPHILE | YIELD Z—Leu Arg—Pro | RATE OF TRANSFOR-MATION | PURITY (by HPLC) |
|---|---|---|---|---|---|---|---|---|---|---|
| 3-8 | 1.25 | DMF - 15° C.<br>10 min + OHBT<br>10 min − 15° C.<br>20 min·0° C. | NHM | 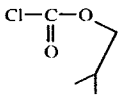 | $NaHCO_3$<br>2 eq. | $DMF/H_2O$<br>80/20 | 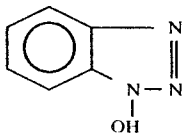 | 85% | 100% | 98% |
| 3-9 | 1.4 | THF - 15° C. | NMM | 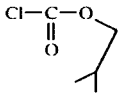 | $NaHCO_3$<br>2 eq. | $DMF/H_2O$<br>90/10 | — | 80% | incomplete | 90%<br>impurities |

DMF - dimethylformamide
THF - tetrahydrofuran
NMM - N-methylmorpholine
OHBT - hydroxybenzotriazol

What is claimed is:

1. A compound of the formula:

L Leucyl - L Arginyl - L Proline.

2. A compound of the formula:

L-Leucyl - L Arginyl - L Proline wherein said compound contains a protecting group other than t-butyloxycarbonyl on at least one of its amine functions.

3. A compound according to claim 2 wherein said protecting group and said at least one amine function form a carbamate.

4. A compound according to claim 2 wherein said protecting group is selected from the group consisting of benzyloxycarbonyl, fluoroenylmethoxycarbonyl, benzoyl, trifluoroacetyl, urethane, formyl, trityl and nitrophenylsulphenyl.

5. A compound according to claim 2 wherein said protecting group is benzyloxycarbonyl.

6. A compound according to claim 2 wherein said L-Leucyl-L-Arginyl-L-Proline is protected on the C-terminal acid function by a protecting group selected from the group consisting of ester groups and primary or nitrogen-substituted amide groups.

7. A compound according to claim 6 wherein said ester group is an alkyl ester wherein the alkyl chain contains from 1 to 20 carbon atoms.

8. A compound according to claim 7 wherein the alkyl chain of said ester group is selected from the group consisting of ethyl, phenyl, benzyl and t-butyl.

9. A compound of the formula:

Leucyl-Arginyl-Proline.

10. A compound of the formula:

R Leucyl-R Arginyl-R Proline.

* * * * *